United States Patent [19]

Michael

[11] Patent Number: 5,110,794
[45] Date of Patent: May 5, 1992

[54] METHOD OF IMMUNIZATION WITH PARTIALLY CATIONIZED SUBSTANCES AND SAID PARTIALLY CATIONIZED SUBSTANCES

[75] Inventor: Jacob G. Michael, Cincinnati, Ohio

[73] Assignee: Abbott Laboratories, Abbott Park, Ill.

[21] Appl. No.: 494,678

[22] Filed: Mar. 16, 1990

Related U.S. Application Data

[63] Continuation-in-part of Ser. No. 147,063, Jan. 22, 1988, which is a continuation-in-part of Ser. No. 9.234, Jan. 30, 1987.

[51] Int. Cl.$^5$ .................... A61K 39/12; C07K 3/00; C07K 13/00
[52] U.S. Cl. .................... 514/2; 530/404; 530/405; 530/806; 424/87; 424/88; 424/89; 424/90; 514/8; 514/10; 514/12
[58] Field of Search ............. 530/350, 389, 390, 391, 530/392, 393, 403, 404, 405, 806, 808; 424/87, 88, 89, 90, 91, 92; 514/2, 8, 10, 21

[56] References Cited

U.S. PATENT DOCUMENTS

| | | | |
|---|---|---|---|
| 3,531,565 | 9/1970 | Webb et al. | 424/89 |
| 3,632,741 | 1/1972 | Wittman et al. | 424/89 |
| 3,651,213 | 3/1972 | Wallis et al. | 424/89 |
| 3,761,585 | 9/1973 | Mullan et al. | 424/89 |
| 3,825,525 | 7/1974 | Mullan et al. | 530/405 |
| 3,893,993 | 7/1975 | Mullan et al. | 530/405 |
| 3,903,067 | 9/1975 | Mullan et al. | 530/405 |
| 4,036,952 | 7/1977 | Bauer et al. | 424/89 |
| 4,185,090 | 1/1980 | McIntire | 530/405 |
| 4,199,565 | 4/1980 | Fullerton | 424/89 |
| 4,314,993 | 2/1982 | Wijnendaele | 530/403 |
| 4,329,281 | 5/1982 | Christenson et al. | 530/405 |
| 4,356,170 | 10/1982 | Jennings et al. | 530/405 |
| 4,395,394 | 7/1983 | Wolff et al. | 424/89 |
| 4,451,446 | 5/1984 | Vandevelde et al. | 424/92 |
| 4,526,716 | 7/1985 | Stevens | 530/403 |
| 4,597,967 | 7/1986 | Beachey | 530/405 |
| 4,691,006 | 9/1987 | Stevens . | |
| 4,701,521 | 10/1987 | Ryser et al. . | |
| 4,705,777 | 11/1987 | Lehrer et al. . | |
| 4,842,862 | 6/1989 | Jacobs et al. | 424/89 |

OTHER PUBLICATIONS

Chu et al. Journal of Immunological Methods. 55 1982 73–78.
Koyama et al., Immunol., 58, 529–540, 1986.
Oite et al., J. Exp. Med., vol. 155, Feb. 1982 460–474.
Border et al., J. Clin. Invest., vol. 69, Feb. 1982, 451–461.
Hoare et al., J. Biol. Chem., vol. 242 (1967), 2447–2453.
Pesce et al., J. Immunol. Meth., 87, (1986) 21–27.

*Primary Examiner*—John Doll
*Assistant Examiner*—Lila Feisee
*Attorney, Agent, or Firm*—Donald O. Nickey; Roger Gilcrest; Frank S. Ungemach

[57] ABSTRACT

A partially cationized protein-containing substance that exhibits enhanced immunogenicity as compared to the native protein-containing substance and is useful in mammalian immunization by oral or parenteral administration.

24 Claims, No Drawings

METHOD OF IMMUNIZATION WITH PARTIALLY CATIONIZED SUBSTANCES AND SAID PARTIALLY CATIONIZED SUBSTANCES

CROSS-REFERENCE TO RELATED APPLICATIONS

This application is a continuation-in-part of application Ser. No. 07/147,063, filed Jan. 22, 1988 which is a continuation-in-part of application Ser. No. 07/009,234, filed Jan. 30, 1987, in the name of Jacob Gabriel Michael.

FIELD OF THE INVENTION

This invention relates to partially cationized protein-containing substances, such as antigens, which possess enhanced immunogenicity and to a method of enhancing the immune response to a native antigen.

BACKGROUND OF THE INVENTION

The importance of antigens in the prevention of infectious disease through immunization is well known. The basis of immunization is the exposure of the animal to be immunized to dead or weakened infectious agents (viruses, bacteria, toxins, etc.) or extracts thereof which contain a foreign, generally macromolecular substance which is capable of evoking an immune response. These substances are generally referred to as antigens.

Most antigens are either wholly or partially composed of protein. The action of antigens is thought to be dependent in part on the antigen's affinity for certain binding sites on cells of the immune system. These cells may be present in blood and internal organs. Interaction of the antigens with the binding site stimulates the immune system which, when actuated, defends the organism against infectious agents.

Antigens can have adverse side effects on the organism sought to be immunized. This is important in the treatment of humans and animals. It is therefore desirable to be able to achieve an effective immunogenic response while utilizing lower levels of an immunogenic antigen. If immunogenicity of an antigen can be increased, a smaller dosage of the antigen can be administered to achieve a given level of immunity.

One way to increase immunogenicity of a substance is by using an adjuvant in conjunction with the substance. An adjuvant is a substance which augments the immune response. Adjuvants can have toxic and other side effects. Thus, adjuvants are generally disfavored for use in humans or in any other organism where toxicity and/or side effects are a concern. The elimination of the need for adjuvant utilization by otherwise increasing immunogenicity of the antigen is therefore desirable.

Some substances do not evoke an immune response at all, or do so very poorly, when brought into contact with cells of the immune system. It would be advantageous to be able to convert such substances from a non-immunogenic form to an immunogenic form. This would allow vaccines to be produced where this was not previously possible.

Immunization is normally carried out by subcutaneous or intramuscular injection of the vaccine. Oral administration of an antigen is not feasible in most instances because it often causes suppression rather than an increase of the immune response. Exceptions to this general rule include live attenuated bacterial and viral vaccines. Oral vaccines offer advantages such as lower expense and ease in administration and packaging. Therefore, it would be advantageous to be able to administer non-live vaccines in oral form.

The catonization of protein-containing substances has been known for some time (see reference 15 below). Several methods of cationizing proteins have been described to modify the protein so as to produce animal models of arthritis and glomerulonephritis. However, none of the prior art has disclosed, suggested or demonstrated enhanced immunogenicity of cationized protein-containing substances.

There has heretofore been no recognition in the prior art that partially cationized antigens can be used in in vivo treatment and prevention of disease. Furthermore, the prior art has not recognized that partially cationized antigens can be used as vaccines. Indeed, it has been reported that cationized proteins do not exhibit enhanced immunogenicity (see reference 9 below).

An aspect of the present invention relates to the discovery that partially cationized antigenic protein-containing substances possess enhanced immunogenic properties. Through this discovery, a method of enhancing immune response to a native antigen is provided.

Other background information is contained in the following references which are hereby incorporated by reference:

1. Barnes, J. and M. Venkatachalam, *Enhancement of Glomerular Immune Complex Deposition by a Circulating Polycation.* J. Exp. Med. 160:286 (1984).

2. Olte, S. P. Batstord, J. J. Mihatson, H. Takamija and A. Vogt, *Quantitative Studies on in situ Immune Complex Glomerulonephritis in the Rat Induced by Planted Cationized Antigen.* J. Exp. Med. 155:460-474 (1982).

3. Gallo, G., Caulen, T. Glaser, S. N. Emancipator and M. E. Lamm, *Nephritogenicity and Differential Distribution of Glomerular Immune Complexes Related to Immunogen Charge.* Lab. Invest. 48:460 (1983).

4. Schikwik, J., W. B. Van den Berg, L. B. A. van de Putte, L. A. B. Joosten & L. van den Bersselaar, *Cationization or Catalase, Peroxidase, and Superoxide Dismutase: Effect or Improved Interarticular Retention on Experimental Arthritis in Mice.* J. Clin. Invest. 76:195 (1985).

5. Muckerheide, A. J. Pesce and J. G. Michael, *Immunosuppressive Properties of a Peptic Fragment of BSA.* J.Immunol. 119:1340 (1977).

6. Dosa, S., A. J. Pesce, D. J. Ford, A. Muckerheide and J. G. Michael, *Immunological Properties as Peptic Fragments of Bovine Serum Albumin.* Immunol. 38:509 (1979).

7. Muckerheide, A., A. J. Pesce and J. G. Michael, *Kinetics of Immunosupporession Induced by Peptic Fragments of Bovine Serum Albumin.* Cell. Immunol. 50:340 (1980).

8. Muckerheide, A., A. J. Pesce and J. G. Michael, *Modulation of the IgE Immune Response to BSA by Fragments of the Antigen.* Cell. Immunol. 59:392 (1981).

9. Border, W. A., H. J. Ward, E. S. Hamil and A. H. Cohen, *Induction of Membranous Nephropathy in Rabbits by Administration of an Exogenous Cationic Antigen.* J. Clin. Invest. 69:451 (1982).

10. Apple, R., B. Knauper, A. J. Pesce and J. G. Michael, *Shared Determinants of Native and Denatured Bovine Serum Albumin are Recognized by Both B- and T-Cells.* Mol. Immunol. 21:901 (1984).

11. Levine, B. B. and N. M. Vaz, *Effect of Combinations of Inbred Strain Antigen and Antigen Dose on Immune Responsiveness and Reagin Production in the Mouse.* Int. Aron. Allergy Appl. Immunol. 39:156 (1970).

12. Ferguson, T. A., T. Peters, Jr., R. Reed, A. J. Pesce and J. G. Michael, *Immunoregulatory Properties of Antigenic Fragments from Bovine Serum Albumin.* Cell. Immunol. 73:1 (1983).

13. Julius, M. H., E. Simpson and L. A. Herzenberg, *A Rapid Method for the Isolation or Functional Thymus-derived Murine Lymohocytes.* Eur. J. Immunol. 3:645 (1973).

14. Hoare, D. G. and D. E. Koshland, *A Method for the Quantitative Modification and Estimation of Carboxylic Acid Groups in Proteins.* J. Biol. Chem. 242:2447 (1967).

15. Danon, D. L. Goldstein, Y. Markovsky and E. Skutelsky, *Use of Cationized Ferritin as a Label or Negative Charges on Cell Surfaces.* J. Ultrastructure Res. 38:500 (1972).

16. Warren, H. S., F. R. Vogel and L. A. Chedid, *Current Status of Immunological Adjuvants.* Ann. Rev. Immunol. 4:369 (1986).

17. Mills, Z. J. and E. Haber, *The Effect on Antigenic Specificity of Changes in the Molecular Structure of Ribonuclease.* J. Immunol. 91:536 (1963).

18. Heber-Katz, E., D. Hansburn and R. H. Schwartz, *The Ia-molecule or the Antigen-presenting Cell Plays a Critical Role in Immune Responses Gene Regulation of T Cell Activation.* J. Mol. Cell. Immunol. 1:3 (1983).

19. Buus, S., and 0. Werdelin, *Oligopeptide Antigens of the Angiotensin Lineage Compete for Presentation by Paraformaldehyde-treated Accessory Cell to T Cells.* J. Immunol. 136:459 (1986).

20. Babbit, B. P., P. M. Allen, G. Matsueda, E. Haber and E. R. Unanue, *Binding of Immunogenic Peptides to Ia Histocompatibility Molecules.* Nature (London) 317:359 (1985).

21. Buus, S., S. Color, C. Smith, J. H. Freed, C. Miles and H. M. Grey, *Interaction Between a "Processed" Ovalbumin Peptide and Ia Molecules.* P.N.A.S. 83:2968 (1986).

22. Larey, E. X., E. Margoliash, F. W. Fitch and S. K. Pierce, *Role of L3T4 and Ia in the Heterocolitic Response of T Cells to Cytochrome.* J. Immunol. 186:3933 (1986).

23. A. N. Glazer, R. J. DeLange and D. S. Sigman, *Chemical Modifications of Proteins. Lab. Techniques in Biochemistry and Mol. Biology,* Vol. 4, Part I, p. 1-205. North-Holland (Am. Elsevier) (1976).

24. Alexander N. Glazer, *The Chemical Modification of Proteins by Group-Specific and Site Specific Reagents.* 1-103. In: *The Proteins.* 3rd ed. Vol. II Acad. Press, N.Y. (1976).

25. A. J. Pesce, R. Apple, N. Sawtell, and J. G. Michael, *Cationic Antigens, Problems Associated With Measurement by ELISA.* J. Immunol, Meth. 87:21 (1986).

26. Unanue, C. R. and J. C. Cerottini, *Antigen Presentation,* The FASEB Journal, 3:2496 (1989).

Where cited herein, these publications are referred to by their numbers in the above list.

SUMMARY OF THE INVENTION

The present invention relates to partially cationized protein-containing substances (PCS) having enhanced immunogenicity as compared to the same native protein-containing substance.

The present invention also relates to a method of immunizing a mammal comprising administering to said mammal an effective amount of a partially cationized protein-containing substance that has enhanced immunogenicity as compared to the corresponding native protein-containing substance. Administration can be oral or parenteral, with or without an adjuvant.

As used herein, "protein-containing substance" includes all proteins, as well as substances whose molecular composition is in some part proteinaceous, such as lipoproteins. These may be substances which do or do not have antigenic properties in their native forms. More specific examples of such substances include, without limitation, bovine serum albumin (BSA), hen egg albumin (OVA), bovine gammaglobulin (BGG), ferritin, bacterial endotoxin, diphtheria toxoid, tetanus toxoid, rotavirus, infectious bursal disease virus, and other microorganisms, including bacteria and viruses and protein-containing products thereof.

As used herein, "cationization" means the conversion, substitution or addition of functional groups to the protein-containing substance whereby the substance is rendered relatively more cationic (positively charged). Such protein containing substances are generally anionic within a physiologic pH range and are converted to, or substituted by, a cationic or nonionic moiety. An example of such a cationization is the reaction whereby anionic side chain carboxyl groups of the PCS are substituted with polycationic aminoethylamide groups.

As used herein, the unreacted or "native" form of the protein-containing substance is indicated by a prefix "n" and the cationized form is indicated by a prefix "c". For example, bovine serum albumin (BSA) may be expressed as "nBSA" for the native form and "cBSA" for the cationized form.

As used herein, the terms "antigen" and "immunogen" mean any substance which is capable of eliciting an immune response. The term "immunogenicity" denotes the immune response to an antigen as determined by assessment of the humoral and/or cellular response to the native molecule. In like fashion, the term "hapten" means any substance which is not immunogenic or poorly immunogenic, and which when conjugated either covalently or ionically to a carrier protein, exhibits increased immunogenicity.

Representative of haptens useful in the instant invention include polysaccharides derived from bacteria, yeast, fungi, and parasites; peptides derived from bacteria, yeast, fungi, and eucaryotes; nucleic acids; hormones; cytokines; and the like.

The present invention is based, in part, on a method of preparing an antigenic protein-containing substance which comprises reacting (1) a protein-containing substance, and (2) a reagent capable of cationizing the protein-containing substance; and halting the reaction between the protein-containing substance and the reagent after a time sufficient to result in partial cationization of the protein-containing substance.

A useful method of cationization involves use of a reagent comprising at least one carbodiimide and at least one amine. Control of the degree of cationization is effected by varying the pH, time of reaction and concentration of the reactants. The reaction may be halted or quenched readily at any desired degree of partial cationization. By way of non-limiting example, the reaction of BSA with a carbodiimide and an amine may be quenched after mean substitution of about 20 of the anionic carboxyl groups with amine groups. The resulting cationic BSA would be partially cationized since a fully substituted BSA could contain about 97 new amino groups based on the amino acid sequence of BSA.

The present invention provides a partially cationized antigenic protein-containing substance having enhanced immunogenicity as compared to the same native protein-containing substance. In general, the partially cationized substance will have an isoelectric point (pI) within the range from about 6.5 to about 9.5, determined by isoelectric focusing as hereinafter described. A partially cationized material is not a single species of cationized material but rather a heterogeneous distribution of species within a range of pI values.

This invention also provides conjugates of the partially cationized proteins with haptens. As conjugates, the haptens evidence enhanced immunogenicity. Haptens, such as polysaccharides, conjugated to a cationized carrier evidence enhanced humoral immunogenicity and the capacity to stimulate a T-cell dependent immune response.

DETAILED DESCRIPTION OF THE INVENTION

The protein-containing substance (PCS) can be cationized by several methods known in the art. (9,15). A preferred method is the reaction of ethylenediamine/1-ethyl-3-(3-dimethylaminopropyl)-carbodiimide (EDC) with the PCS. This reaction involves the activation of the carboxyl groups of a protein with carbodiimide and the subsequent reaction of the activated carboxyl group with a nucleophile of the general type +R-NHz to obtain the primary amine derivatives. Considerable versatility can be achieved since both the chemical nature of the modification, i.e. introduction of primary, secondary or tertiary amine groups and the degree of modification of the protein carboxyl groups can be varied by proper choice of reagents, reaction time and pH of the coupling reaction.

The cationization methods suitable for use in the present invention are those which effect cationization under mild reaction conditions. As used herein, mild reaction conditions are those under which the molecular character (e.g. 1°, 2° or 3° structure) of the subject PCS is not substantially altered so as to adversely affect its immunogenicity. These conditions can be generally described as relatively low temperature and low ionic strength and are neither very acidic (e.g. below pH 4) nor basic (e.g. above pH 8) and do not present an extreme oxidative or reductive environment.

The pH of the EDC reaction is generally maintained in the range from about 4.75 to about 6.25. More rapid substitution of carboxyl groups in the EDC reaction occurs at the lower pH levels within this general range.

Reaction time is determined by the concentration of the reactants and by the degree of cationization desired. Representative reaction times range from about 2 minutes to about 120 minutes.

The reaction is maintained within the general range from about 4° C. to about 37° C. and is generally maintained at about 25° C.

Each known method of cationization may be halted or quenched according to several methods known in the art. Such quenching prevents further addition of cationic groups to the PCS thereby facilitating the production of molecules with the desired level of cationization. The EDC reaction is quenched with a buffer, preferably an acetate buffer, which terminates the reaction. Concentration of the acetate buffer is about 4M.

Cationization can be verified and quantified using gel electrophoresis as hereinafter described, isoelectric focusing techniques known in the art, zeta potential measurements as hereinafter described and other chemical methodologies (14).

The protein-containing substance is cationized to an extent whereby it exhibits enhanced immunogenic character. It is within the skill of the art to determine and adjust the degree of cationization which increases the antigenic character for all PCS types including those which may fall outside the 6.5 to 9.5 pI range.

The following Examples are intended to illustrate the present invention as practiced on several antigens. Variations of the parameters and methodology for optimization of the present invention for any specific PCS is within the skill of the artisan.

EXAMPLE 1

Bovine Serum Albumin (nBSA), five times crystallized, was cationized according to the general procedure described by Border (9).

Five grams of nBSA was dissolved in distilled water to a volume of 25 ml and admixed with a solution of ethylene diamine (EDA) in 500 ml distilled water for a final EDA concentration of $1\underline{M}$. The pH of this solution was adjusted to about 4.75 with $6\underline{N}$ HCl. To this was added 1.8 grams of 1-ethyl-3-(3-dimethylaminopropyl)-carbodiimide (EDC).

The reaction was permitted to proceed for varying periods of time (5 min.–120 min.), with constant stirring, while the temperature was maintained at about 25° C. and the pH was held constant. After quenching with $4\underline{M}$ acetate buffer, the reaction mixture was subjected to multiple dialysis treatments against distilled water and lyophilized. It was then chromatographed through Sephadex G-25 and lyophilized again before use.

EXAMPLE 2

The method of Example 1 was further modified to show how changes in reaction conditions (i.e., time, pH and molar ratios) can be used to achieve comparable levels of EDA substitution on BSA.

In general, the cationization was accomplished as follows: A solution of $1\underline{M}$ ethylenediamine (EDA) in 10 mM 2-(N-morpholino) ethanesulfonic acid (MES) was prepared by dissolving 53.2 g EDA dihydrochloride (Sigma) and 0.79 g MES (Sigma) in 365 ml of deionized water (Milli-Q system by Millipore) in a polyethylene or polypropylene container, and the pH adjusted as desired. The final volume was 400 ml. To this was added 2.0 g of "ultrapure" BSA (Boehringer/Mannheim). The solution was stirred continuously in a constant temperature water bath at 25° C. until the BSA was dissolved. At this point, a 50 ml sample was removed, mixed with 1.5 ml of pH adjusted $4\underline{M}$ acetic acid to match the pH of the reaction. This sample was used as a time zero sample for later comparisons. The reaction was then initiated with the addition of 1-ethyl-3-[(dimethylaminopropyl)carbodiimide hydrochloride] (EDC, Pierce) dissolved in 10 ml of deionized water. The reaction solution was stirred continuously, maintaining temperature and pH. At selected time intervals, 50 ml samples were removed and mixed with 1.5 ml of pH adjusted $4\underline{M}$ acetic acid to quench the reaction. Upon completion of the reaction, all samples were allowed to incubate with the acetic acid for 1 hour at room temperature. The samples were then placed in dialysis bags (Spectra-Por, MW cut-off 14,000). All samples were dialyzed together against two 20-liter volumes of 10 mM sodium phosphate, pH 7.2; four 20-liter volumes of 10 mM sodium phosphate, 150 mM sodium chloride, pH 7.2; and two 20-liter volumes of deionized water. All dialyses were performed at 4° C. for a minimum of 8 hours each. The samples were stored in polypropylene containers at 4° C.

EXAMPLE 3

The method of Example 1 was repeated with the exception that the PCS used was native hen egg albumin (OVA) (purchased from Sigma Chemical Co., St. Louis, Mo.) instead of nBSA. OVA was cationized at pH 5.0 for 60 minutes.

EXAMPLE 4

The method of Example 1 was repeated with the exception that the PCS used was bovine gamma globulin (BGG) (purchased from Sigma Chemical Co., St. Louis, Mo.). Cationization was performed as in Example 1 except that the reaction was stopped after 30 minutes.

EXAMPLE 5

Diphtheria toxoid (DT) (purchased from Connaught Laboratories) contained 11.7 mg protein and 3000 Lf/ml (Lf is a standard flocculating unit). It was cationized under conditions similar to those described for BSA in Example 2 with the following differences. The pH of the reaction was 5.5, and the EDC/DT molar ratio was 250. The times of cationization were 0, 2, 5, 20, 45, 80, 120, and 180 minutes.

EXAMPLE 6

The method of Example 1 was repeated with the exception that the PCS used was native tetanus toxoid (TT) instead of nBSA (Lederle Laboratories, Pearl River, N.Y.) and the cationization reaction was terminated after 30 minutes.

EXAMPLE 7

The method of Example 1 was repeated with the exception that the PCS used was ferritin (purchased from Sigma Chemical Co., St. Louis, Mo.), samples of which were cationized for 5 minutes, 15 minutes and 30 minutes.

EXAMPLE 8

The method of Example 1 was repeated with the exception that the PCS used was E.coli bacteria (0127) (from American Type Cell Collection, Washington, D.C.). Bacteria were cultured for 16 hours, washed and killed by boiling for 10 minutes. Bacteria were again washed three times with saline prior to cationization for 15 minutes.

EXAMPLE 9

Simian rotavirus (SA-11) was grown in cell culture and purified in a cesium chloride gradient. It was then cationized under conditions described for BSA in Example 2. The pH of the reaction was 4.75, the EDC content was 0.36 mg EDC/mg protein, and the cationization times were 0, 5, 20, 60, and 120 minutes. The rotavirus protein concentration was 1.8 mg/ml.

EXAMPLE 10

Infectious bursal disease virus (IBDV) was grown in cell culture and inactivated with formalin. It was cationized under conditions as described for BSA in Example 2 with the following differences. The EDC concentration was 0.36 mg EDC/mg protein, the pH of the reaction was 4.75, and the cationization times were 15, 30 and 60 minutes.

EXAMPLE 11

A bacterial endotoxin or lipopolysaccharide (LPS) was prepared from E. coli 055:B5 which was purchased from Difco Laboratories, Detroit, Mich. The LPS was cationized using the procedure of Example 1. Although extensively purified, it contained 1.5 percent residual protein. The pH was 4.75, the EDC concentration was 0.36 mg/mg LPS, and the cationization times were 15, 30, 60 and 120 minutes.

EXAMPLE 12

The method of Example 1 was repeated with the exception that fluorescein isothiocyanate (FITC) (purchased from Sigma Chemical Co.), a non-immunogenic molecule, was conjugated either to nBSA carrier or to a cBSA carrier (as prepared in Example 1). These covalent conjugates were used as the PCS.

The FITC conjugation method was as follows: FITC was used in 0.5 mg concentration per mg BSA. FITC was added to BSA solution and the pH was adjusted to about 8.4 with borate buffer. The conjugation was allowed to proceed for about 1 hour with continuous mechanical stirring at slow speed. The suspension was dialyzed in a cold room with frequent changes of saline adjusted to a pH of about 7.8 with borate buffer. The dialysis required several days and was complete when the dialyzate was virtually free of yellow-green color under ultraviolet light. The conjugate was clarified by centrifugation.

Other hapten-carrier conjugations may require more complex chemical reactions to achieve covalent bonding between the reacting molecules.

EXAMPLE 13

The method of Example 1 was used to cationize BSA and the reaction was terminated at 60 minutes. Pneumococcal capsular polysaccharide type III (SIII) was obtained from Dr. P. Baker of NIAID, Bethesda, Md. and non-covalently bound to the cBSA.

BSA, cationized as described in Example 1 for 60 minutes, was dissolved in distilled $H_2O$ at a concentration of 200 µg/ml. Purified capsular polysaccharide was also dissolved in water at 200 µg/ml and mixed with nBSA or cBSA at a ratio of 5 ml to 1 ml which produces a final protein to polysaccharide ratio of 1:4. A fine white precipitate formed immediately upon mixing and particles continued to aggregate during an overnight incubation at room temperature. The precipitate was isolated by centrifugation at 300×g, washed 3 times with $dH_2O$ and air dried. Complexes were characterized for protein concentration and polysaccharide content. The complexes contain approximately 75% cBSA and 25% polysaccharides.

Prior to immunization, complexes were dissolved in PBS at pH 9 and sterilized by millipore filtration.

Analytical Methods

Isoelectric Focusing

Samples of cBSA have been analyzed by isoelectric focusing in the PHAST system (Pharmacia) using conditions specified by the manufacturer. The standard curve obtained for isoelectric point (pI) determinations used Sigma standards ranging from a pI of 3.5-9.3. The gels show that a number of cBSA species are present in each sample, appearing as a broad smear covering a range of pI's. Several bands within this broad range can be distinguished.

The products were determined to have an isoelectric point greater than 6.5 and up to about 9.5. The change or increase in isoelectric point is used as one of the measures to determine the degree to which a given PCS has been cationized.

EDA Determination

The cationization of antigens covalently couples EDA to the anionic carboxyl groups of the protein containing antigen. The number of ethylenediamine additions was determined in hydrolyzed samples of cationized BSA and other antigens. Concentrated hydrochloric acid, Baker Ultrex, was used for preparation of 6N HCl for hydrolysis. Lithium diluent, pH 2.2 (Pickering Laboratories) was used as a sample and standard diluent.

A standard of ethylenediamine dihydrochloride (Aldrich) was prepared by dissolving approximately 26 mg in 50 ml of pH 2.2 lithium diluent yielding a solution of approximately 3.9 mM. A standard of arginine was prepared by dissolving approximately 17.4 mg of arginine in 100 mL of pH 2.2 lithium diluent, yielding a solution of approximately 1 mM. A dilute standard was prepared from these solutions by diluting 3.0 mL of the ethylenediamine (EDA) standard and 10.0 mL of the arginine standard to 50 mL with pH 2.2 lithium diluent.

The following reagents were used for the post-column derivatization and chromatographic analysis. All reagents were supplied by Pickering Laboratories unless noted otherwise: lithium eluents, 2.75 pH (Li275), lithium column regenerant (RG003), and trione, ninhydrin reagent. A modified lithium regenerant was prepared by adding lithium chloride to the Pickering regenerant. (This solution was used when necessary to sharpen the ethylenediamine peak). A solution of approximately 5M lithium chloride (Pierce) was prepared by dissolving approximately 21 mg of lithium chloride in 100 mL of reagent grade water (supplied by Lab Five Reagent Grade Water Preparation System from Technics). 25 mL of this solution was combined with 175 mL of the regenerant yielding a solution approximately 0.89N lithium.

Sample hydrolysis was performed using a Pierce Reacti-Therm Heating Module. Chromatograms were obtained using a Dionex BioLC Amino Acid Analyzer equipped with an AutoIon Reagent Controller, ninhydrin post-column derivatization unit, an IonChrom UV/Vis detector with a NIN filter, and an Automated Sampler Module. The analytical column used consists of a Pickering Lithium Guard Column, 3×20 mm P/N 0373020.

An accurately known weight (or volume) of sample equivalent to 1-4 mg was transferred to a screw-capped glass culture tube. If the sample was dry, 1 mL of reagent grade water was added. An equivalent volume of concentrated HCl was added, and the tube vortexed briefly to mix the contents. The tube was placed in a heating module and hydrolyzed for 24 hours at approximately 100° C. The contents were transferred to a 50 ml round bottom flask, the tube rinsed several times with 1 ml of reagent grade water, and the rinsings added to the flask. The hydrochloric acid and water were removed using a rotary-evaporator, high vacuum and a water bath at approximately 60°-80° C. Approximately 5 ml of reagent grade water was added and the evaporation repeated twice. After the final evaporation, the sample was reconstituted with an accurately known volume of pH 2.2 lithium diluent using a volume five times the sample starting volume. After filtering the sample through a 0.45 micron filter to remove any solids, it was placed in an autosampler vial.

The Amino Acid Analyzer is configured to inject a fixed volume (20 microliters) of standard and sample. The following eluent profile is used to chromatograph the EDA.

TABLE 1

| Time | Flow* | % Li750 | % RG003 |
|---|---|---|---|
| 0.0 | 0.3 | 100 | 0 |
| 5.0 | 0.3 | 100 | 0 |
| 35.0 | 0.3 | 89 | 11 |
| 35.1 | 0.3 | 100 | 0 |
| 44.0 | 0.3 | 100 | 0 |

*mL/min

Trione reagent has a continuous flow at approximately 0.3 mL/min.

Calculation of results were performed against the dilute standard EDA and arginine solution. Both percent EDA (by weight) and EDA/Arg molar ratio were determined, the latter being used as an internal standard for the sample analyzed. The calculations are shown below:

$$\% \text{ EDA} = \frac{\text{Area of EDA (sample)}}{\text{Area of EDA (STD)}} \times$$

$$\text{mM EDA (std)} \times 5 \text{ mL} \times \frac{60.10 \text{ mg/mmole} \times 1 \text{ L}}{1000 \text{ mL} \times \text{mg of sample}} \times 100$$

EDA/Arg Molar Ratio =

$$\frac{[\text{Area of EDA (sample)}/\text{Area of EDA (STD)}] \times \text{mM EDA (std)}}{[\text{Area of Arg (sample)}/\text{Area of Arg (std)}] \times \text{mM Arg (std)}}$$

Zeta Potential

Electrophoretic mobilities were determined using a DELSA 440 (Coulter Electronics) which is an analytical instrument based on laser Doppler velocimetry (LDV). LDV determines the speed of particles by analyzing the Doppler frequency shifts of scattered light relative to the detector at a fixed position. The extent of the Doppler shift in frequency is directly proportional to the velocity of the moving particle. The zeta potential of the particles is derived from their electrophoretic mobilities through the use of the Debye-Huckel equation.

All of the zeta-potential data was acquired at a temperature of 25° C., pH of 7.0, ionic strength of 0.15, conductivity of 18.490 mS/cm, a viscosity of 0.00890 poise and a dielectric constant of 78.360. Under these conditions a constant voltage of 15 volts was applied across the sample chamber, a run time of 120 seconds, an analysis time of 2 seconds and a relaxation (off) time of 0.5 seconds between each run was employed. In addition to the multiple runs per sample, each sample was also analyzed at least in triplicate. Thus each of the data points represents the average of many hundred individual electrophoretic mobility measurements.

Immunologic Methods

Experimental Animal: Except where otherwise noted $BDF_1$ mice were used for all studies. Mice 6-10 weeks of age were purchased from the Jackson Laboratory, Bar Harbor, Me. Each experimental group consisted of 5 mice and each experiment was repeated at least twice.

Adjuvants: Complete and incomplete Freund's adjuvant (IFA) and bacterial lipopolysaccharide were purchased from Difco Laboratories, Detroit Mich. Aluminum hydroxide gel was prepared according to the method of Levine and Vaz (11) or was in the form of commercial Maalox (Rorer Inc., Fort Washington, Pa.).

Antibody Measurement: For determination of antibody titers to nBSA, an enzyme linked immunsorbent assay (ELISA) was used. Polystyrene microtiter plates were coated with 100 µl of 50 µg/ml native antigen in coating buffer (2.9 g $NaHCO_3$, 0.2 g sodium azide, Q.S. to 1 liter distilled water, pH 9.5-9.7). Before use and in between steps, the plates were washed with tap water on an automatic plate washer, 5 cycles, 350 µl/well with 15 second intervals. Wells were filled with 100 µl of test antiserum or control/standard sera diluted in serum/conjugate diluent (2% fish gelatin, 2% Tween-20, 0.011% thimerosal, Q.S. to 1 liter PBS). Positive control sera was a pool of anti-nBSA hyperimmune $BDF_1$ mouse sera (titer=90 mg anti-BSA antibody per milliliter) diluted to 1:5000 in normal mouse sera. After incubation for 1 hour, covered at room temperature (RT), the plates were washed and filled with 100 µl/well of a peroxidase labeled, affinity purified goat antimouse IgG (H+L chain) diluted to 1/5000 in serum/conjugate diluent, incubated for 1 hour at room temperature and washed. One hundred µl/well of Chromogen (O-Phenylenediamine 2 HCL) were added and allowed to react for 25 minutes at room temperature. The reaction was stopped with 100 µl/well of 1N $H_2SO_4$ and read immediately in an ELISA reader at 490 nanometers. Results were expressed as µg of anti-BSA antibody per milliliter of serum.

A quantitative ELISA technique (12) was also used to assay the response to various other antigens. Standard curves were established each time an assay was performed, using known amounts of antibody raised in response to either native or cationized antigen available. Variations are described in the Tables below where applicable.

T Cell proliferation assays: $BDF_1$ mice were injected in the hind footpads and tail base with 100 µg native antigen emulsified in IFA. The inguinal and popliteal lymph nodes were removed 10 days later and the subsequent cell suspension was passed over a nylon wool column as has been described (13). The nylon wool non-adherent cells were then resuspended in complete RPMI 1640 medium containing 10% horse serum, 1 mM nonessential amino acids, 1 mM sodium pyruvate, 2 mM glutamine, $5 \times 10^{-5}M$ 2-mercaptoethanol, 25 mM HEPES and 5 µg/ml gentamicin, and plated in 96 well flat bottom plates (Costar, Cambridge, Mass.) at $5 \times 10^5$ cells/well. Native or cationized antigen was added at various concentrations in serum-free complete RPMI 1640 to triplicate wells. Serum-free medium served as a control. Cells were incubated in a final volume of 200 µl at 37° C. with 5% $CO_2$ for 72 hours at which time 1 µCi $^3$H-thymidine was added to each well. Cells were harvested 20 hours later using a Skatron harvester and radioactivity was determined by liquid scintillation spectrophotometry.

Evaluation of Cationization Reaction Conditions

The pH, reaction time and EDC were varied independently to determine the effect of each variable on the level of cationization. Tables 2-5 list the reaction conditions examined and the results of the EDA analysis of BSA samples prepared as described in Example 2. Each set of reaction conditions is designated alphabetically, along with the pH of the reaction, and the molar ratio of EDC to BSA. The reaction time points are listed in the first column, and range from $t=0$ to $t=120$ minutes. The second, fourth and sixth columns list the results of the EDA analysis, expressed as the molar ratio of EDA to arginine (ARG) found in the samples. An alternate expression is given in the third, fifth and seventh columns, in which the known arginine content of BSA (23 arginine residues per BSA molecule) has been used to calculate the average level of modification, expressed as the molar ratio EDA/BSA. In experiments N and O (Table 5) all reactions were allowed to proceed for 120 minutes and the molar ratio of EDC/BSA was increased to high levels in order to identify the maximum level of EDA/BSA that could be obtained.

The cationization reaction can be controlled by controlling the pH of the reaction and the concentration of EDC. At a particular pH, the level of modification is directly related to the EDC/BSA used in the reaction. A comparison of the rate curves at each pH shows that increasing the pH requires a greater amount of EDC to achieve the same level of modification. Also, at higher pH (Table 4, Experiment K, L, M), the initial reaction is much faster, and not sustained as long as at a lower pH. This is consistent with the degradation, or auto-hydrolysis of EDC at higher pH. Since EDC is consumed more rapidly at higher pH, more carbodiimide is required to reach a given level of modification, and the reaction proceeds initially at a higher rate, then slows.

The rate of modification under Example 2 conditions (Table 2 experiment C) has been analyzed by a calculated first-order comparison. Under these conditions, the reaction is 90-100% complete by 120 minutes, with the limit of incorporation at 49 EDA/BSA (mean molar ratio).

An analysis of the extent of modification verses the amount of EDC used under the various conditions of pH was undertaken. At pH 4.75 and 5.5, the level of EDC/BSA has been extended to determine the limits of modification (Table 5). These analyses show a direct relationship of EDC concentration to degree of modification at 120 minutes, and may be used to target any desired degree of modification. The results also show that under non-denaturing conditions, at either pH 4.75 or 5.5, the maximum level of modification achievable is 79 EDA/BSA. This may be compared to a theoretical potential of 97, based on the amino acid content of BSA (aspartate+glutamate residues=96+the carboxy terminus (1)=97).

Danon (15) recognized the importance of pH of the coupling reaction upon the extent of protein modification by water soluble carbodiimides. The results of the current experiments show that the combination of selected pH and the concentration of carbodiimide and time of reaction provide control of the extent of modification. The apparent upper limit of 79 EDA residues incorporated into non-denatured BSA has been demonstrated at two reaction conditions.

TABLE 5-continued

| EDC/BSA | EDA/ARG | #EDA/BSA |
|---|---|---|
| 1125 | 3.43 | 79 |

TABLE 2

| | A pH 4.75; EDC/BSA = 30 | | B pH 4.75; EDC/BSA = 60 | | C Standard Conditions pH 4.75; EDC/BSA = 125 | |
|---|---|---|---|---|---|---|
| Time | EDA/ARG | #EDA/BSA | EDA/ARG | #EDA/BSA | EDA/ARG | #EDA/BSA |
| 0 | 0 | 0 | 0 | 0 | 0 | 0 |
| 5 | 0.12 | 2.8 | 0.19 | 4.4 | 0.44 | 10.1 |
| 10 | 0.18 | 4.1 | 0.34 | 7.8 | 0.72 | 16.6 |
| 15 | 0.22 | 5 | 0.45 | 10.4 | 0.94 | 21.6 |
| 20 | 0.28 | 6.4 | 0.54 | 12.4 | 1.08 | 24.8 |
| 30 | 0.37 | 8.5 | 0.69 | 15.9 | 1.36 | 31.3 |
| 60 | 0.46 | 10.6 | 0.99 | 22.8 | 1.78 | 40.9 |
| 120 | 0.59 | 13.6 | 1.15 | 26.5 | 2.13 | 49 |

TABLE 3

| | D pH 5.5; EDC/BSA = 30 | | E pH 5.5; EDC/BSA = 60 | | F pH 5.5; EDC/BSA = 125 | |
|---|---|---|---|---|---|---|
| Time | EDA/ARG | #EDA/BSA | EDA/ARG | #EDA/BSA | EDA/ARG | #EDA/BSA |
| 0 | 0 | 0 | 0 | 0 | 0 | 0 |
| 5 | 0.003 | 0.07 | 0.06 | 1.3 | 0.18 | 4.1 |
| 10 | 0.044 | 1 | 0.11 | 2.5 | 0.26 | 6 |
| 15 | 0.05 | 1.1 | 0.13 | 3 | 0.32 | 7.4 |
| 20 | 0.072 | 1.7 | 0.2 | 4.6 | 0.39 | 9 |
| 30 | 0.11 | 2.5 | 0.24 | 5.5 | 0.5 | 11.5 |
| 60 | 0.17 | 3.9 | 0.4 | 9.2 | 0.78 | 17.9 |
| 120 | 0.28 | 6.4 | 0.61 | 14 | 1.1 | 25.3 |

| | G pH 5.5; EDC/BSA = 250 | | H pH 5.5; EDC/BSA = 500 | |
|---|---|---|---|---|
| Time | EDA/ARG | #EDA/BSA | EDA/ARG | #EDA/BSA |
| 0 | 0 | 0 | 0 | 0 |
| 5 | 0.4 | 9.2 | 0.76 | 17.5 |
| 10 | 0.51 | 11.7 | 0.96 | 22 |
| 15 | 0.64 | 14.7 | 1.13 | 26 |
| 20 | 0.75 | 17.3 | 1.27 | 29.2 |
| 30 | 0.91 | 20.9 | 1.5 | 34.5 |
| 60 | 1.31 | 30.1 | 1.95 | 44.9 |
| 120 | 1.7 | 39.1 | 2.41 | 55.2 |

TABLE 4

| | I pH 6.25; EDC/BSA = 60 | | J pH 6.25; EDC/BSA = 125 | | K pH 6.25; EDC/BSA = 250 | |
|---|---|---|---|---|---|---|
| Time | EDA/ARG | #EDA/BSA | EDA/ARG | #EDA/BSA | EDA/ARG | #EDA/BSA |
| 0 | 0 | 0 | 0 | 0 | 0 | 0 |
| 5 | 0.04 | 0.09 | 0.128 | 4.1 | 0.28 | 6.4 |
| 10 | 0.047 | 1.1 | 0.131 | 2.5 | 0.32 | 7.4 |
| 15 | 0.051 | 1.2 | 0.15 | 3.5 | 0.35 | 8.1 |
| 20 | 0.06 | 1.4 | 0.18 | 4.1 | 0.4 | 9.2 |
| 30 | 0.08 | 1.8 | 0.21 | 4.8 | 0.42 | 9.7 |
| 60 | 0.11 | 2.5 | 0.29 | 6.7 | 0.56 | 11.5 |
| 120 | 0.17 | 3.9 | 0.38 | 8.7 | 0.7 | 16.1 |

| | L pH 6.25; EDC/BSA = 500 | | M pH 6.25; EDC/BSA = 1000 | |
|---|---|---|---|---|
| Time | EDA/ARG | #EDA/BSA | EDA/ARG | #EDA/BSA |
| 0 | 0 | 0 | 0 | 0 |
| 5 | 0.59 | 13.6 | 1.15 | 26.5 |
| 10 | 0.63 | 14.5 | 1.2 | 27.6 |
| 15 | 0.67 | 15.4 | 1.26 | 29 |
| 20 | 0.72 | 15.4 | 1.29 | 29.7 |
| 30 | 0.77 | 17.7 | 1.38 | 31.7 |
| 60 | 0.97 | 22.3 | 1.57 | 36.1 |
| 120 | 1.23 | 28.3 | 1.84 | 42.3 |

TABLE 5

| EDC/BSA | EDA/ARG | #EDA/BSA |
|---|---|---|
| N (pH 4.75; Time = 120 Minutes) | | |
| 125 | 2.33 | 53 |
| 375 | 3.18 | 73 |
| O (pH 5.5; Time = 120 Minutes) | | |
| 500 | 2.48 | 57 |
| 1500 | 3.29 | 75.7 |
| 4500 | 3.45 | 79.4 |

The isoelectric focusing migration distances and determined pI values of the dominant bands for BSA cationized as described in Table 2 experiment C at pH 4.75, EDC/BSA 125 and 0–120 minutes are presented in Table 6. In the pI range of 4.9 to 8.7, distinguishable dominant bands are also observed, however, minor species are observed at higher pI values. By 120 minutes of reaction time, most of the protein migrates from the gel, which has an end point of pI 9.3. This 120 minute sample corresponds to BSA cationized as described by Border (9).

TABLE 6

Dominant Bands of Cationized BSA

| Sigma Standards | | | pI Measurements* Reaction Time (minutes) | | | | | | |
|---|---|---|---|---|---|---|---|---|---|
| Dist. (mm) | pI | nBSA | 5 | 10 | 15 | 20 | 30 | 60 | 120 |
| 1.5 | 3.55 | 4.75 | 4.9 | 5.1 | 5.6 | 7.3 | 7.8 | 8.2 | >9.3 |
| 6.5 | 4.55 | | 5.1 | 5.3 | 6.2 | 7.8 | 8.2 | 8.4 | |
| 10 | 5.13 | | 5.3 | 5.7 | 6.5 | 8.2 | 8.3 | 8.7 | |
| 14.5 | 5.85 | | 5.4 | 6.2 | 7.6 | 8.3 | 8.5 | | |
| 19 | 6.57 | | 5.7 | 6.5 | 8.2 | 8.5 | 8.7 | | |
| 20.5 | 6.76 | | 6.2 | 7.3 | 8.25 | 8.7 | | | |
| 25 | 7.16 | | 6.5 | 7.6 | 8.3 | | | | |
| 33 | 8.4 | | 7.2 | 7.8 | 8.7 | | | | |
| 34 | 9.1 | | 7.25 | 8.3 | | | | | |
| 36 | 9.3 | | | 8.7 | | | | | |

A comparison of the EDA, pI, and immunogenicity data for cBSA cationized under conditions described by Border (9) as well as representative partially cationized cBSA of the present invention is made in Table 7. It is clear that the cationization time of 120 minutes (Border) results in a higher level of cationization (EDA/BSA molar ratio of 41.9) and suboptimal immunogenicity. The cationization times of 15 and 30 minutes produce a cBSA with significantly greater immunogenicity and a lower level of cationization (EDA/BSA molar ratio of 16–24).

TABLE 7

Comparison of cBSA Analytical and Immunogenicity Data

| BSA | EDA/BSA | pI Range of Dominant Bands | Immuno-genicity* |
|---|---|---|---|
| nBSA | 0 | 4.75 | 424. ± 420 |
| 15'-cBSA (Example 1) | 15.9 | 5.6–8.7 | 5257 ± 2228 |
| 30'-cBSA (Example 1) | 23.7 | 7.8–8.7 | 3007 ± 1034 |
| 120'-cBSA-Border (Example 1) | 41.9 | >9.3 | 1252 ± 416 |

*Data taken from Table 9 of experiment evaluating "Immune Response to cBSA With and Without Alum"

Immunologic Studies

Immune Response to a Single Dose of cBSA with Alum

Table 8 demonstrates that the level of cationization of BSA (as determined by duration of the cationization reaction) affects the level of antibody produced against native BSA. Antibody levels rise in response to cationization until an optimal level of modification is achieved. Increased modification beyond this point leads to a significantly diminished antibody response.

TABLE 8

| | Antibody Response to cBSA | |
|---|---|---|
| Time of Cationization | Antigen Species | Anti-BSA µg of IgG/ml |
| None | nBSA | 350 |
| 15 min. | cBSA | 1220 |
| 30 min. | cBSA | 1450 |
| 60 min. | cBSA | 1135 |
| 120 min. | cBSA | 110 |

Cationization was conducted at pH 4.75 and 25° C.; mice were injected intraperitoneally (i.p.) with 50 µg antigen in 1 mg alum; anti nBSA response was measured at day 14.

Immune Response to cBSA with and Without Alum

The cBSA was prepared as described in Example 1. The cationization times used were 0, 5, 15, 30, 60, and 120 minutes.

100 µg nBSA or cBSA was suspended in PBS or PBS plus 1 mg of alum in the form of Maalox ®. This mixture was injected i.p. The immunization dose was given on day 0, and the booster dose (identical to the immunization dose) was given on day 24. All animals were bled prior to immunization and bled again eleven days after booster (day 35 of the experiment).

TABLE 9

Antibody Response to cBSA in Alum Adjuvant

| Antigen | | Anti-BSA (µg IgG/ml ± SD) |
|---|---|---|
| nBSA | | 424.6 ± 920.4 |
| cBSA, | 5' | 3836.5 ± 1165.5 |
| cBSA, | 15' | 5257.5 ± 2228.4 |
| cBSA, | 30' | 3006.6 ± 1034.7 |
| cBSA, | 60' | 1786.2 ± 582.6 |
| cBSA, | 120' | 1252.6 ± 416.8 |

Data in Table 9 show a clear improvement of the anti-BSA serum titer by cBSA given in alum adjuvant. There was a maximal improvement in the immune response to the 15 minutes cBSA. The other cBSA preparations were also effective, but to a lesser degree.

TABLE 10

Antibody Response to cBSA in PBS without Alum

| Antigen | | Anti-BSA (IgG µg/ml ± SD) |
|---|---|---|
| nBSA | | 9.5 ± 8.5 |
| cBSA, | 5' | 79.9 ± 72.1 |
| cBSA, | 15' | 195.5 ± 37.5 |
| cBSA, | 30' | 160.6 ± 97.5 |
| cBSA, | 60' | 76.2 ± 63.9 |
| cBSA, | 120' | 94.4 ± 41.1 |

Table 10 shows cBSA injected in PBS alone (no alum added). In this experiment the immune response was also clearly enhanced by cationization of the antigen; and the maximal effect was observed in groups receiving the 15 or 30 minutes preparations.

The data in Table 8 shows the immune response of mice immunized with one dose of 50 µg cBSA as compared to data in Tables 9 and 10 for mice immunized with two doses of 100 µg cBSA. In all cases with alum and without, one or two doses, the cBSA showed enhanced immunogenicity compared to nBSA.

Statistical Analysis: As the observed levels of immune response were overwhelmingly greater for the groups using alum as an adjuvant, comparisons of groups of differing cationization times were made separately for the groups receiving alum and those groups which did not. To compare the six cationization times, a multiple comparison procedure was selected that was appropriate for equal sample sizes and would control the experimental error rate. The procedure used was described by Welsch [Welsch, R. E. (1977), *Stepwise Multiple Comparison Procedures*, Journal of the American Statistical Association, 72, 359].

Analysis of the mice receiving BSA with alum demonstrated that the groups with cationization times of 5, 15, and 30 minutes all had statistically significantly greater immune response at the 0.05 level than the group receiving native BSA (Table 9). The 15-minute group had the greatest mean immune response, and it was significantly greater than all other groups receiving alum.

The results for the mice not receiving alum as an adjuvant were similar though the immune response was much lower for each cationization time (Table 10). Again, the greatest response was in the group given BSA cationized for 15 minutes. The immune response of this group was significantly greater than that of all groups, except the 30 minute group. These results suggest that the maximum level of immune response to cBSA requires between 15 and 30 minutes of cationization time. These data showed that cationization of the antigen stimulated the antibody response to a higher degree than the native antigen with and without alum.

TABLE 11

Physical Chemical Characterization of cBSA Samples

| Antigen | EDA/BSA | EDA/ARG | Z Potential | pI Range |
|---------|---------|---------|-------------|----------|
| nBSA | 0.0 | 0.00 | −9.6 | 4.75 |
| cBSA, 5' | 8.5 | 0.37 | −5.6 | 4.9–7.25 |
| *cBSA, 15' | 15.9 | 0.69 | −3.2 | 5.6–8.7 |
| *cBSA, 30' | 23.7 | 1.03 | +1.6 | 7.8–8.7 |
| cBSA, 60' | 33.4 | 1.46 | +5.0 | 8.2–8.7 |
| cBSA, 120' | 41.9 | 1.82 | +10.5 | >9.3 |

*partially cationized cBSA with optimal immune response as reported in tables 9 and 10.

Data in Table 11 shows that EDA and zeta potential measurements reflect an increase in positive charges experienced by the antigen when exposed for varying lengths of time to the cationization reaction. There is a clear correlation between the improvement of the immune response and the incremental increase of positive charge at lower levels of EDA additions. It is important to note that excessive EDA additions and number of positive charges render the antigen less immunogenic.

An important observation from the isoelectric focusing data (Table 6) is that a given cBSA preparation, partially modified, does not contain a single species of cBSA, but a variety of species with a range of pI values. Although these populations can be characterized by determining the mean EDA incorporation, it should be noted that the actual preparation is heterogeneous. Therefore, the enhanced immunogenicity observed for a given preparation is most likely due to the optimal production of a range of cBSA species which together elicit the desired response. The pI of these various species showing enhanced immunogenicity generally fall within the range of 6.5–9.5.

Thus the above experiments have demonstrated the following:

1. BSA cationized for 15 to 30 minutes, under the abovementioned conditions, represented an optimal preparation to be used as an immunogen.

2. Partial cationization of the antigen proved to be immunologically beneficial, and excessive numbers of positive charges to the molecule rendered their immunogenic properties less than optimal. Hence, there was an optimal cationization level that produced the maximal immune response.

Effect of Cationization on Lymphocyte Response to Bovine Serum Albumin.

TABLE 12 cBSA Induced Proliferation of Primed Lymphocytes

| Time Cationization | Antigen Specie | Relative Lymphocyte Stimulation |
|--------------------|----------------|--------------------------------|
| None | nBSA | ++ |
| 15 min. | cBSA | +++ |
| 30 min. | cBSA | ++++ |
| 60 min. | cBSA | +++ |
| 120 min. | cBSA | − |

Lymphocytes obtained from $BDF_1$, mice and primed in vivo with nBSA were stimulated in vitro with either nBSA or multiple forms of cBSA as described in Methods. Table 12 demonstrates that cationization (at pH 4.75, EDC/BSA=125) for up to 60 minutes enhances the ability of the antigen to stimulate lymphocyte proliferation primed by the native antigen. Excessive cationization (i.e. 120 min.) renders the cBSA less active.

Effect of Pretreatment with Native or Cationized Antigen on Subsequent Immunization Mice were inoculated intravenously with physiological saline or varying doses of nBSA or cBSA (cationization at pH 4.75; EDC/BSA=125; 30 minutes reaction) on 3 consecutive days 1 week prior to intraperitoneal immunization with 100 μg nBSA or cBSA in 1 mg alum as adjuvant. Antibody (IgG) levels against nBSA were assayed at 10 and 21 days post intraperitoneal immunization.

The effect of the pretreatments are expressed in terms of enhancement (+) or suppression (−) of the antibody response relative to controls which received intravenous pretreatment with saline only.

TABLE 13

Effect of Pretreatment on Antibody Response to BSA

| Pretreatment nBSA | Immunization 100 μg nBSA | | Pretreatment cBSA | Immunization 100 μg nBSA | |
|---|---|---|---|---|---|
| | 10d | 21d | | 10d | 21d |
| 1 μg | 0 | 0 | 1 μg | ++ | +++ |
| 10 μg | = | 0 | 10 μg | +++ | ++++ |
| 25 μg | = | − | 25 μg | ++ | ++ |
| 100 μg | − | = | | | |

| Pretreatment nBSA | Immunization 100 μg cBSA | | Pretreatment cBSA | Immunization 100 μg cBSA | |
|---|---|---|---|---|---|
| | 10d | 21d | | 10d | 21d |
| 1 μg | 0 | 0 | 1 μg | ++++++++ | |
| 10 μg | 0 | 0 | 10 μg | +++ | +++ |
| 25 μg | − | 0 | 25 μg | ++ | ++ |
| | | | 100 μg | ++++ | ++ |

IgG antibody levels to nBSA were measured and compared to IgG levels in mice which received a pretreatment of physiologic saline only. Data are reported as relative suppression: (−)15–50% of control, (=)50–100% of control; relative enhancement: (+)0–100% control, (++)100–500% control, (+++)500–1000% control, (++++)>1000% control; or no significant change (0) less than or equal to 15% suppression.

As anticipated by the works of others (see H. N. Eisen, *General Immunology*, p. 143 J. B. Lippincott, N.4. (1990) and M. F. Saklayen, A. J. Pesce, V. E. Pollak and J. G. Michael, *Kinetics of Oral Tolerance: Study of Vari-* ables *Affecting Tolerance Induced by Oral Administration of Antigen,* Int. Arch. Allergy and App. Immun. 73:5 (1984), Table 13 shows that i.v. pretreatment with appropriate doses of nBSA (i.e. ≧10 μg) results in a diminution of the immune response to i.p. administered nBSA. On the other hand, pretreatment with cBSA (1 μg to 100 μg) enhanced the response to subsequent immunization with either cBSA or nBSA.

To extend the observation of Table 13, pretreatment with nBSA or cBSA was administered orally. Mice were fed 20 mg/day on 3 subsequent days, one week prior to i.p. immunization with nBSA or cBSA. IgG response to nBSA was measured on days 10, 14 and 24 and the results are reported in Table 14(a). Native hen egg albumin (nOVA) was cationized as described in Example 3. Mice were fed 20 mg/day of nOVA or cOVA on 3 subsequent days one week prior to i.p. immunization with 0.1 μg antigen in 1 μg alum. The immune response was measured at 14 days post immunization and is reported in Table 14(b).

TABLE 14a

Effect of Pretreatment on Antibody Response to BSA

| Oral Pretreatment | Immunization | anti nBSA IgG (μg/ml) | | |
|---|---|---|---|---|
| | | 10d | 14d | 24d |
| — | nBSA | 900 | 814 | 240 |
| nBSA | nBSA | 87 | 58 | 57 |
| nBSA | cBSA | 250 | 287 | 675 |
| — | cBSA | 1024 | 2076 | 3050 |
| cBSA | nBSA | 2700 | 1074 | 875 |
| cBSA | cBSA | 3700 | 6300 | 6300 |

TABLE 14b

Effect of Pretreatment on Antibody Response to OVA

| Oral Pretreatment (20 mg Antigen/Dose) | 10 μg Antigen in 1 mg Alum | anti nOVA (μg/ml) |
|---|---|---|
| — | nOVA | 140 |
| nOVA | nOVA | 35 |
| nOVA | cOVA | 100 |
| — | cOVA | 765 |
| cOVA | nOVA | 1320 |
| cOVA | cOVA | 2250 |

From this data it is concluded that while oral administration of native antigen may inhibit subsequent immunization with either native or cationized antigen, a similar administration of cationized antigen primes the animals for an enhanced response to either form of the antigen.

Immune Response to cOVA and nOVA

As is apparent from Table 14, appropriately cationized hen egg albumin elicits a higher level of antibody production than its native counterpart. Table 15 demonstrates an antibody dose response to increasing levels of nOVA or cOVA immunization. Mice were inoculated with the indicated dose of nOVA or cOVA (cationized as above) in 1 mg alum. Antibodies to nOVA were measured by ELISA at 9, 14 and 21 days post immunization.

TABLE 15

Antibody Response to OVA

| Antigen Administered i/p with 1 mg Alum | Response (μg/ml Anti-nOVA Antibodies) | | |
|---|---|---|---|
| | 9d | 14d | 21d |
| 0.1 μg nOVA | 80 | 120 | 120 |

TABLE 15-continued

Antibody Response to OVA

| Antigen Administered i/p with 1 mg Alum | Response (μg/ml Anti-nOVA Antibodies) | | |
|---|---|---|---|
| | 9d | 14d | 21d |
| 0.1 μg cOVA | 425 | 976 | 770 |
| 1.0 μg nOVA | 450 | 840 | 660 |
| 1.0 μg cOVA | 1300 | 2010 | 1660 |
| 10 μg nOVA | 1250 | 1420 | 1300 |
| 10 μg cOVA | 1500 | 2350 | 3200 |

Table 15 verifies that cOVA is a more effective antibody inducer than nOVA although both antigens evoke a dose dependent response. The data also demonstrate that the difference between the cationic and native antigen-induced response diminishes at higher doses.

Tables 16, 17, 18 and 19 demonstrate the consistent effect of appropriate cationization on the immunogenicity of a variety of purified protein antigens.

Effect of Cationization on Immunogenicity of BGG

Bovine gamma globulin (BGG) (purchased from Sigma Chemical Co., St. Louis, Mo.) was cationized as described in Example 4 and the reaction stopped at 30 minutes. Mice were immunized by intraperitoneal injection of indicated doses of BGG in 1 mg alum and bled at various time intervals. Anti-nBGG antibody levels were measured by ELISA and column purified anti-BGG antibodies were used as standards.

TABLE 16

Antibody Response to BGG

| Immunization | Anti-BGG antibodies μg/ml | | |
|---|---|---|---|
| | 9 days | 14 days | 21 days |
| 1 μg nBGG | 55 | 80 | 60 |
| 1 μg cBGG | 110 | 180 | 180 |
| 10 μg nBGG | 110 | 400 | 800 |
| 10 μg cBGG | 450 | 1200 | 1600 |
| 50 μg nBGG | 350 | 850 | 1000 |
| 50 μg cBGG | 1200 | 2500 | 2500 |
| 100 μg nBGG | 320 | 1200 | 1200 |
| 100 μg cBGG | 850 | 2100 | 2600 |

Table 16 demonstrates that partial cationization increases the immunogenicity of bovine gamma globulin.

The Effect of Cationization on Immunogenicity of Diphtheria Toxoid.

Diphtheria toxoid (DT) was cationized as described in Example 5. Mice were immunized i.p. with either 1 Lf or 10 Lf doses of native or cationic DT with alum. The immunizing dose was given on day 0 and the same dose was given as a booster on day 14. All animals were bled prior to immunization and at 14 days after the booster dose on day 28. The antibody was measured in an ELISA assay with native DT as antigen on the microtiter plate. The results are expressed as geometric mean antibody titers.

The analytical data for the cationized DT is shown in Table 17 (a). There is an increase in surface charge (pI range) and an increase in EDA additions with increasing time of cationization.

TABLE 17(a)

| Treatment Groups | cDT Analytical Data | |
|---|---|---|
| | EDA/DT Molar Ratios | EDA/Arginine |
| Native | 0 | 0 |

TABLE 17(a)-continued

| | cDT Analytical Data | |
|---|---|---|
| Treatment Groups | EDA/DT Molar Ratios | EDA/Arginine |
| 2 min. | 2.56 | 0.16 |
| 5 min. | 4.32 | 0.27 |
| 20 min. | 7.2 | 0.45 |
| 45 min. | 12.48 | 0.78 |
| 80 min. | 15.84 | 0.99 |
| 120 min. | 20.32 | 1.27 |
| 180 min. | 22.08 | 1.38 |

TABLE 17(b)

Antibody Response to cDT

| | Geometric Mean Antibody Titers | | | | | |
|---|---|---|---|---|---|---|
| Dose | Native | 2 min. | 20 min. | 45 min. | 80 min. | 180 min. |
| 1 Lf unit | 1166 | 1750 | 2236* | 1192 | 836 | 207 |
| 10 Lf units | 3314 | 4909* | 3396 | 3567 | 3044 | 1410 |

*Mean titers significantly higher than native diphtheria toxoid.

The immunogenicity of the cationic and native DT is shown in Table 17(b). The cationic DT given at the 1 Lf dose showed significantly enhanced immunogenicity with the 20 min. cationization sample while the 10 Lf dose of cationic DT showed significantly enhanced immunogenicity with the 2 minute cationization sample.

Effect of Cationization on Immunogenicity of Tetanus Toxoid

Tetanus toxoid (TT) (provided by Lederle Labs., Pearl River, N.Y.) was cationized as described in Example 6. Mice were inoculated intraperitoneally with either nTT or cTT in the doses indicated in 1 mg alum and bled at various time intervals. Antibody levels to nTT were determined by ELISA.

TABLE 18

Antibody Response to cTT

| | Anti-tetanus antibody (Percent enhancement over nTT (control)) | | |
|---|---|---|---|
| Immunization | 14 d | 28 d | 35 d |
| 1 μg cTT | 220 | 300 | 320 |
| 10 μg cTT | 325 | 560 | 720 |
| 100 μg cTT | 280 | 450 | 660 |

Table 18 shows marked enhancement of immunogenicity of partially cationized tetanus toxoid over the native material.

Effect Of Cationization On The Immunogenicity Of Ferritin

Cationized ferritin was produced as described in Example 7. 100 μg of each cationized ferritin sample was administered i.p. to mice. Antibody levels at days indicated were measured by ELISA on plates coated with native ferritin.

TABLE 19

Antibody Response to Cationized Ferritin

| Bled at days | Percent Enhancement over N Ferritin (control) | | |
|---|---|---|---|
| | 5 min. | 15 min. | 30 min. |
| 9 | 169 | 97 | 217 |
| 15 | 134 | 101 | 490 |
| 21 | 122 | 123 | 241 |
| 35 | 195 | 206 | 457 |

Table 19 shows an increase in immunogenicity of variously cationized ferritin.

Effect of Cationization on the Immunogenicity of Heat Killed Bacteria

*E. coli* 055 were cationized as in Example 8 then rewashed 3 times. The cell numbers indicated were injected i.p. into mice without adjuvant. The mice were bled at designated times. Antibody concentration was determined by ELISA in which plastic plates were coated with untreated bacteria. Antibacterial antibody titers in mice immunized with untreated bacteria served as controls and were compared with antibody titers from mice immunized with cationized bacteria.

TABLE 20

Antibody Response to Cationized *E. coli*

| No. of bacteria injected | Percent enhancement over controls | | |
|---|---|---|---|
| | 10 days | 20 days | 30 days |
| $1 \times 10^6$ | 160 | 210 | 180 |
| $5 \times 10^6$ | 220 | 450 | 650 |
| $1 \times 10^7$ | 260 | 500 | 460 |
| $5 \times 10^7$ | 320 | 800 | 650 |

Table 20 shows that all cationized bacterial doses tested produce an increase in immunogenicity over untreated bacteria.

The Effect of Cationization on Rotavirus Immunogenicity

The simian rotavirus SA-11 was purified by cesium chloride gradient centrifugation, inactivated with binary ethyleneimine and cationized as described in Example 9. Pathogen free CF-1 mice were immunized with the native and cationized rotavirus at doses of 0.1 μg, 1.0 μg, and 10 μg without adjuvant. The cationization times used were 20 and 60 minutes. The immunizing dose was given intraperitoneally and subcutaneously on day 0, and the same dose was repeated as a booster on day 14. All animals were bled prior to immunization and bled again 14 days after the booster, day 28 of the experiment. The antibodies were measured in an ELISA assay using purified native SA-11 rotavirus as the antigen on microtiter plates. The results are expressed as mean titers of antibody activity.

The analytical data from the rotavirus preparation is shown in the following table. There is an increasing surface charge (zeta potential) and an increase in number of EDA additions with higher cationization times.

TABLE 21(a)

| Cationic Rotavirus Analytical Data | | | |
|---|---|---|---|
| Cationization Time | zeta Potential | % EDA | Molar Ratio |
| native (control) | −16.7 | 0 | 0 |
| 0 time | −13.5 | 0 | 0 |
| 5 min. | −11.2 | 0.18 | 0.07 |
| 20 min. | −9.6 | 0.30 | 0.13 |
| 60 min. | −7.4 | 0.30 | 0.13 |
| 120 min. | −4.9 | 0.35 | 0.16 |

The immunogenicity of the cationized rotavirus antigen is shown in Table 21(b). The 1 μg and 10 μg doses shown an enhanced immunogenicity with both i.p. and subcutaneous (sc) administration of the cationized antigen over the native antigen.

TABLE 21(b)

| | Antibody Response to Cationic Rotavirus | | | | | |
|---|---|---|---|---|---|---|
| | Geometric Mean Antibody Titers Treatment Groups | | | | | |
| Route | Native | | 20 min. | | 60 min. | |
| Dose | i.p. | sc | i.p. | sc | i.p. | sc |
| 10.0 μg | 27,669 | 16,384 | 201,720 | 65,536 | 194,040 | 65,536 |
| 1.0 μg | 13,568 | 4,096 | 24,730 | 16,384 | 54,274 | 16,384 |
| 0.1 μg | 2,920 | 1,024 | 3,521 | 4,096 | 3,031 | 4,096 |

The Effect of Cationization on Immunogenicity of Infectious Bursal Disease Virus (IBDV)

The IBDV used in this experiment was cell culture derived and inactivated with formalin. It was cationized as described in Example 10. Six week old white leghorn chickens were immunized subcutaneously with native IBDV and IBDV cationized for 15, 30, and 60 minutes. The dose was 3 mg protein in either aluminum hydroxide or oil emulsion. All birds were bled prior to immunization and weekly for 3 weeks. The antibodies were measured in an ELISA assay using native IBDV as antigen on the microtiter plate and the results are expressed as titers of antibody activity.

The analytical data for the cationized IBDV is shown in Table 22(a). There is an increase in surface charge (zeta potential) and an increase in EDA additions with increased time of cationization.

TABLE 22(a)

| | Cationic IBDV Analytical Data | | |
|---|---|---|---|
| IBDV | EDA % | EDA/ARG | ZETA POTENTIAL |
| Native | — | — | −34.76 |
| 15' | 0.30 | 0.67 | −27.68 |
| 30' | 0.33 | 0.68 | −24.35 |
| 60' | 0.30 | 0.73 | −20.41 |

TABLE 22(b)

| | Antibody Response to Cationic IBDU | | | | |
|---|---|---|---|---|---|
| | | | Weeks Post Inoculation Antibody Titers | | |
| Vaccine | n | Preinoc | 1 | 2 | 3 |
| A10H-native | 4 | 6 ± 0 | 85 ± 79 | 31 ± 18 | 46 ± 37 |
| A10H-15 min. | 4 | 173 ± 164 | 97 ± 55 | 480 ± 171 | 749 ± 281 |
| A10H-30 min. | 4 | 21 ± 15 | 263 ± 187 | 440 ± 202 | 728 ± 487 |
| A10H-60 min. | 4 | 96 ± 76 | 270 ± 148 | 57 ± 28 | 209 ± 71 |
| OIL-native | 4 | 37 ± 23 | 76 ± 62 | 374 ± 295 | 987 ± 805 |
| OIL-15 min. | 4 | 84 ± 31 | 227 ± 118 | 1,487 ± 615* | 1,358 ± 494 |
| OIL-30 min. | 4 | 124 ± 59 | 128 ± 53 | 912 ± 474 | 1,701 ± 371 |
| OIL-60 min. | 4 | 70 ± 64 | 314 ± 178 | 653 ± 232 | 1,804 ± 490 |
| None | 5 | 60 ± 32 | 48 ± 25 | 26 ± 12 | 3 ± 1 |

*indicates significant difference (p < .05) from native vaccine of same adjuvant formulation within sample day using 1-way ANOVA T-test (LSD).

The immunogenicity of the cationic IBDV is shown on Table 22(b). The cationic IBDV was more immunogenic than the native IBDV and was significantly different with the 15 minute cationization specimen 2 weeks after immunization in an oil emulsion.

The overall trend 3 weeks after immunization is for enhanced immunogenicity with all three cationization times given with either alum or oil emulsion.

Immunogenicity of Cationized Bacterial Endotoxin (LPS)

Bacterial endotoxin (LPS) was cationized as in example 11. $BDF_1$ mice (10 mice/group) were immunized i.p. with native and cationized LPS at 10 μg/dose without adjuvant on day 0. All animals were bled prior to immunization and on days 10, 14, 21, 28, 42, 48 and 55 after immunization. Antibodies were measured in an ELISA assay using native LPS as antigen on the microtiter plates. The results as set forth in Table 23 are expressed as O.D. values after standardization against the nLPS response at day 15.

The immunogenicity data on the cationized LPS is shown in Table 23. The 15 minute cationization time shows enhanced immunogenicity over the native LPS, while the 120 minute cationization time sample shows depressed immunogenicity when compared to native LPS.

TABLE 23

| | Antibody Response to cLPS | | | | |
|---|---|---|---|---|---|
| | Anti-nLPS Antibody O.D. values | | | | |
| Days | Native | 15' | 30' | 60' | 120' |
| 10 | 225 | 450 | 146 | 137 | 122 |
| 15 | 280 | 585 | 190 | 176 | 126 |
| 22 | 269 | 576 | 226 | 286 | 198 |
| 28 | 230 | 630 | 221 | 314 | 185 |
| 41 | 370 | 710 | 296 | 452 | 225 |
| 48 | 274 | 602 | 292 | 361 | 193 |
| 55 | 291 | 575 | 328 | 415 | 234 |

Immunogenicity of Haptens Conjugated to Cationic Carrier Proteins

Cationized protein containing substances can also be used to confer enhanced immunogenicity on poorly immunogenic or nonimmunogenic molecules. This enhancement can be observed in humoral as well as cellular responses.

Immunogenicity of FITC Conjugated to cBSA

FITC-BSA conjugates were prepared as described in Example 12. Immune response was determined by measuring the antibodies produced against FITC-nBSA or FITC-cBSA on ELISA plates coated with nFITC (conjugated to keyhole limpet haemocyanin to facilitate molecule for plate attachment).

Table 24 shows that this hapten (FITC) becomes more immunogenic when conjugated to a partially cationized carrier protein (cBSA) as compared to one conjugated to a native protein.

TABLE 24

| Antibody Response of FITC Conjugated to cBSA | |
|---|---|
| Bled at days | % enhancement over FITC-nBSA (control) |
| 10 | 240 |
| 15 | 280 |
| 22 | 330 |

TABLE 24-continued

Antibody Response of FITC Conjugated to cBSA

| Bled at days | % enhancement over FITC-nBSA (control) |
|---|---|
| 30 | 180 |
| 37 | 160 |

Immunogenicity of Pneumococcal Polysaccharide Conjugated to cBSA

Capsular polysaccharide antigens of gram-positive and gram-negative bacteria produce a thymus independent immune response. Used as immunogens in mammals, they usually induce only a primary response which cannot be boosted by repeated injections. (Coen Benvery et al., *Comparison of the Induction of Immunoglobulin M and G Antibodies in Mice with Purified Pneumotoccal Type 3 and Meningococcal Group C Polysaccharides and Their Protein Conjugates,* Infection and Immunity (1982) pp 15–22). When conjugated to a protein carrier, however, the immune response to the polysaccharide can be greatly enhanced. The response becomes thymus dependent and a secondary response can be elicited.

When negatively charged free polysaccharides are mixed with positively charged cationized BSA, a noncovalently bonded complex is formed as described in Example 13.

Balb/c mice were immunized with 0.5 μg SIII without adjuvant or SIII-cBSA complexes with or without incomplete Freund's adjuvant (IFA). Mice were primed at day 0 and challenged at day 40. IgG-specific antibody response to SIII was measured by ELISA at regular intervals over a 98 day period.

As shown in Table 25 (a), this complex induces an enhanced primary antibody response to polysaccharide, and a secondary IgG response as well.

TABLE 25(a)

Anti-Pneumococcal Polysaccharide Antibody Expressed As O.D.

| Dose | Days After Immunization | | | | | | |
|---|---|---|---|---|---|---|---|
| | 15 | 28 | 35 | 42 | 56 | 77 | 98 |
| 100 μg complex (SIII + cBSA) in IFA | 100 | 270 | 460 | 480 | 410 | 1130 | 520 |
| 25 μg SIII only in IFA | 90 | 100 | 120 | 100 | 290 | 370 | 230 |

The T cell proliferation assay was used to evaluate the cellular immunogenicity of SIII complexes. In these experiments, mice were immunized with either 10 μg SIII complex or 2.5 μg SIII. Ten days later, lymph node cells from the immunized mice were removed and incubated with 2.5 μg SIII, 10 μg SIII complex or 100 μg SIII complex in the presence of $^3$H-thymidine. The results are shown in Table 25(b).

TABLE 25(b)

T-Cell Proliferation Expressed as Counts/Min. (CPM)

| Antigen Dose | Mice Primed With | |
|---|---|---|
| | 10 μg Complex (SIII + cBSA) | 2.5 μg SIII |
| SIII 2.5 μg | 22,950 cpm | 1,760 cpm |
| Complex 10 μg (SIII + cBSA) | 5,040 cpm | 1,460 cpm |
| Complex 100 μg (SIII + cBSA) | 51,300 cpm | 2,890 cpm |

The mice primed with the ionic complex of SIII-cBSA show increased T-cell proliferation when incubated with either SIII or SIII complex. These results demonstrate enhanced cellular immunogenicity of the SIII hapten cationic carrier complex as compared to mice primed with SIII alone.

It is observed that both covalent and noncovalent coupling of haptens to a cationic carrier protein induces enhanced humoral and cellular immune responses to both the hapten and the carrier complexes.

The invention has been described in detail with particular reference to preferred embodiments thereof, but it will be understood that variations and modifications can be effected within the spirit and scope of the invention.

What is claimed is:

1. In a method of immunization of an animal against a protein-containing substance comprising administration of said protein-containing substance to the animal in an amount effective to induce an immune response to said protein-containing substance, the improvement consisting essentially of: modifying the protein containing substance through the covalent attachment of at least one agent selected from the group consisting of primary amines, secondary amines, tertiary amines, and ammonium groups, where a) said modified protein-containing substance has an isoelectric point, as measured by isoelectric focusing in a polyacrylamide gel, of at least 0.5 units greater than the isoelectric point of the native, unmodified protein-containing substance, but not in excess of a value of about 9.3;
   b) said modified protein-containing substance is essentially non-reactive at physiological pH; and
   c) the immunological response of the animal to the modified protein-containing substance is greater than to the unmodified, native protein-containing substance.

2. The method according to claim 1, wherein said modified protein-containing substance has an isoelectric point value within the range of from about 4.9 to about 9.3.

3. The method according to claim 1, wherein said modified protein-containing substance is administered with an adjuvant.

4. The method of claim 1 wherein said protein-containing substance is chosen from the group consisting of bovine serum albumin, hen egg albumin, bovine gamma globulin, ferritin, bacterial endotoxin, viral proteins, tetanus toxoid, diphtheria toxoid, rotavirus, infectious bursal disease virus, and killed microorganisms and protein-containing products derived from said substances.

5. The method according to claim 1 wherein said modified protein-containing substance is conjugated with a hapten and wherein the immunological response of the animal to the hapten, conjugated to a modified protein-containing substance is ionically greater than to the hapten, conjugated to the unmodified, native protein containing substance.

6. The method of claim 5, wherein said hapten is selected from the group consisting of bacterial polysaccharides, viral peptides and hormonal peptides.

7. A method of enhancing the immune response of an animal to an unmodified, protein-containing antigen consisting essentially of;

a) covalently modifying the antigen to render it more cationic through use of an agent selected from the group consisting of primary amines, secondary amines, tertiary amines, or ammonium groups so that
   i. the isoelectric point of the modified antigen is increased by at least 0.5 units;
   ii. the isoelectric point of the modified antigen is less than 9.3;
   iii. the modified antigen is essentially non-reactive at physiological pH; and
   iv. the modified antigen induces a stronger immunological response than the unmodified antigen;
b) parenterally administering said modified antigen to said animal such that an immune response is effected; and
c) thereafter parenterally administering said native or modified antigen to said animal such that an enhanced immune response is effected.

8. The method according to claim 7 wherein said modified antigen has an isoelectric point value within the range of from abut 5.6 to about 9.3.

9. The method of claim 7 wherein said native antigen is chosen from the group consisting of bovine serum albumin, hen egg albumin, bovine gamma globulin, ferritin, bacterial endotoxin, viral proteins, tetanus toxoid, diphtheria toxoid, rotavirus, infectious bursal disease virus, and killed microorganisms and protein containing products derived from said substances.

10. The method of claim 7 wherein said modified protein-containing antigen is ionically conjugated with a hapten.

11. The method of claim 7 wherein said hapten is selected from the group consisting of bacterial polysaccharides, viral peptides and hormonal peptides.

12. A protein-containing substance selected from the group consisting of bovine serum albumin, hen egg albumin, bovine gamma globulin, ferritin, bacterial endotoxin, viral proteins, tetanus toxoid, diphtheria toxoid, rotavirus, infectious bursal disease virus, and killed microorganisms and protein-containing products derived from said substances, covalently modified with an agent selected from the group of primary amines, secondary amines, tertiary amines and ammonium groups to render it more cationic than the native protein-containing substance and wherein:

a) the agents introduced are substantially non-reactive at physiological pH;
b) the modified protein-containing substance has an isoelectric point value, as determined by isoelectric focusing at least 0.5 units greater than the native protein-containing substance's native isoelectric point value; and
c) the modified protein-containing substance has an isoelectric point value, as determined by isoelectric focusing, not in excess of a value of about 9.3.

13. A protein-containing substance according to claim 12 wherein the protein-containing substance is bovine serum albumin and the modified protein-containing substance has an isoelectric point value of from about 5.6 to 9.3.

14. A protein-containing substance according to claim 12 wherein the protein-containing substance is diphtheria toxoid and the modified protein-containing substance has an isoelectric point value at least 2.0 pI units greater than the protein-containing substance's native isoelectric point value.

15. A protein-containing substance according to claim 12 wherein the protein-containing substance is rotavirus and the modified protein-containing substance possesses a zeta potential of greater than −10.0.

16. A protein-containing substance according to claim 12 wherein the protein-containing substance is infectious bursal disease virus and the modified protein-containing substance possesses a zeta potential of greater than −28.0.

17. A protein-containing substance according to claim 12 wherein said modified protein-containing substance is ionically conjugated with a hapten.

18. A protein-containing substance according to claim 17 wherein the hapten is selected from the group consisting of bacterial polysaccharides, viral peptides and hormonal peptides.

19. A protein-containing substance according to claim 17 wherein said modified protein-containing substance is conjugated with a polysaccharide hapten and has the capacity to stimulate a T-cell dependent immune response to the hapten.

20. A method of enhancing the immune response of a mammal to a unmodified protein-containing antigen consisting essentially of:

a) covalently modifying the protein-containing antigen to render it more cationic through use of an agent selected from the group consisting of primary amines, secondary amines, tertiary amines, or ammonium groups so that
   i. the isoelectric point of the modified antigen is increased by at least 0.5 units;
   ii. the isoelectric point of the modified antigen is less than 9.3;
   iii. the modified antigen is essentially non-reactive at physiological pH; and
   iv. the modified antigen induces a stronger immunological response than the unmodified antigen;
b) parenteral administration of the modified protein-containing antigen.

21. A method according to claim 20 wherein the covalent modification is effected by coupling the agent to the antigen through an amide bond.

22. The method of claim 20 wherein the increase in isoelectric point value of said modified antigen over the isoelectric point value of said native antigen is at least 0.5 isoelectric point units.

23. A method for increasing the levels of antibodies produced by an animal in response to immunization with an unmodified protein-containing substance, comprising immunization of the animal with a modified protein-containing substance of claim 12.

24. A method according to claim 23 wherein the cationized protein-containing substance is ionically conjugated with a hapten and wherein the level of antibodies produced by the animal to the conjugated hapten-modified protein-containing substance is greater than to the hapten conjugated to the unmodified protein-containing substance.

* * * * *